(12) United States Patent
Black et al.

(10) Patent No.: US 11,967,036 B2
(45) Date of Patent: Apr. 23, 2024

(54) DYNAMIC REGISTRATION OF ANATOMY USING AUGMENTED REALITY

(71) Applicant: MEDIVIEW XR, INC., Cleveland, OH (US)

(72) Inventors: John Black, Bowling Green, OH (US); Greg A. Miller, Findlay, OH (US); Mina S. Fahim, New Brighton, MN (US); Glenn Raudins, Chagrin Falls, OH (US)

(73) Assignee: MEDIVIEW XR, INC., Cleveland, OH (US)

( * ) Notice: Subject to any disclaimer, the term of this patent is extended or adjusted under 35 U.S.C. 154(b) by 102 days.

(21) Appl. No.: 17/320,705

(22) Filed: May 14, 2021

(65) Prior Publication Data
US 2021/0358228 A1 Nov. 18, 2021

Related U.S. Application Data

(60) Provisional application No. 63/025,604, filed on May 15, 2020, provisional application No. 63/025,436, filed on May 15, 2020.

(51) Int. Cl.
*G06T 19/20* (2011.01)
*A61B 5/055* (2006.01)
(Continued)

(52) U.S. Cl.
CPC .............. *G06T 19/20* (2013.01); *A61B 5/055* (2013.01); *A61B 5/0873* (2013.01); *A61B 5/318* (2021.01);
(Continued)

(58) Field of Classification Search
CPC ....... A61B 5/055; A61B 5/0873; A61B 5/318; A61B 6/032; A61B 8/08; A61B 2090/365;
(Continued)

(56) References Cited

U.S. PATENT DOCUMENTS 6,417,861 B1 7/2002 Deering et al.
10,478,255 B2 11/2019 West et al.
(Continued)

FOREIGN PATENT DOCUMENTS

FR 2883718 A1 * 10/2006 ........... A61N 5/1048
WO 2019/152269 A1 8/2019

OTHER PUBLICATIONS

LeCorre (machine translation of FR2883718; Date filed Apr. 4, 2005; Date published Oct. 6, 2006). (Year: 2006).*
(Continued)

*Primary Examiner* — Sing-Wai Wu
(74) *Attorney, Agent, or Firm* — Jacob M. Ward; Ward Law Office LLC

(57) ABSTRACT

A system for dynamic registration of autonomy using augmented reality can include an augmented reality system, an imaging system, a measuring system, and a computer system. The augmented reality system can be configured to display an augmented representation. The imaging system can be configured to image an anatomical feature of the patient and can generate anatomical imaging data. The measuring system can be configured to measure an anatomical movement of the patient and can generate an anatomical movement data. The computer system can be configured to receive the anatomical imaging and positional data and the anatomical movement data, generate the augmented representation based on the anatomical imaging data, associate the augmented representation with the anatomical movement data, render the augmented representation on the augmented reality system, and selectively update the augmented representation based on the anatomical movement data.

20 Claims, 9 Drawing Sheets

Figure 1:
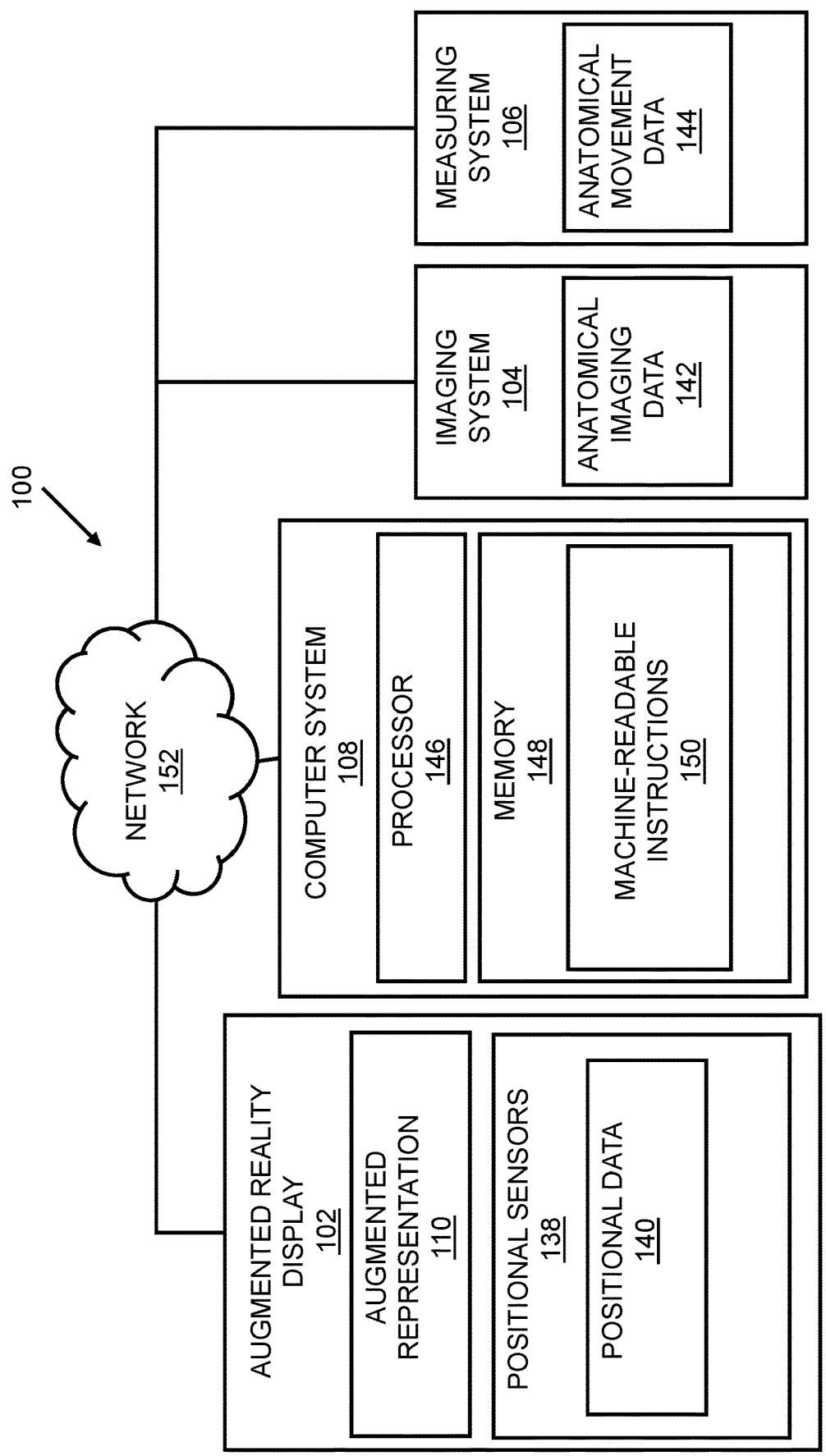

(51) Int. Cl.
*A61B 5/087* (2006.01)
*A61B 5/318* (2021.01)
*A61B 6/03* (2006.01)
*A61B 8/08* (2006.01)
*A61B 90/00* (2016.01)
*G06T 5/00* (2006.01)
*G06T 7/33* (2017.01)
*G06T 19/00* (2011.01)

(52) U.S. Cl.
CPC ............... *A61B 6/032* (2013.01); *A61B 8/08* (2013.01); *G06T 5/002* (2013.01); *G06T 7/33* (2017.01); *G06T 19/006* (2013.01); *A61B 2090/365* (2016.02); *G06T 2207/10081* (2013.01); *G06T 2207/10088* (2013.01); *G06T 2207/10132* (2013.01); *G06T 2207/20221* (2013.01); *G06T 2207/30004* (2013.01)

(58) Field of Classification Search
CPC ....... G06T 19/006; G06T 19/20; G06T 5/002; G06T 7/33; G06T 2207/10081; G06T 2207/10088; G06T 2207/10132; G06T 2207/20221; G06T 2207/30004
See application file for complete search history.

(56) References Cited

U.S. PATENT DOCUMENTS

| | | |
|---|---|---|
| 10,869,727 B2 | 12/2020 | Yanof et al. |
| 10,895,906 B2 | 1/2021 | West et al. |
| 2006/0095047 A1* | 5/2006 | de la Barrera ........ A61F 2/4657 606/102 |
| 2013/0279825 A1 | 10/2013 | Liao et al. |
| 2014/0350571 A1* | 11/2014 | Maillet ................. A61B 34/32 901/8 |
| 2016/0302747 A1* | 10/2016 | Averbuch ............. A61B 6/5235 |
| 2017/0091977 A1 | 3/2017 | West |
| 2017/0360512 A1* | 12/2017 | Couture ................ A61B 34/30 |
| 2018/0256132 A1* | 9/2018 | Halmann ............... A61B 8/488 |
| 2019/0167352 A1 | 6/2019 | Mahfouz |
| 2021/0081035 A1 | 3/2021 | West et al. |
| 2021/0161612 A1 | 6/2021 | Black et al. |
| 2021/0169587 A1 | 6/2021 | Martin, III et al. |
| 2021/0236209 A1 | 8/2021 | Black et al. |
| 2021/0298836 A1 | 9/2021 | Black et al. |

OTHER PUBLICATIONS

Written Opinion of the International Search Authority dated Aug. 31, 2021.

* cited by examiner

DYNAMIC REGISTRATION OF ANATOMY USING AUGMENTED REALITY

CROSS REFERENCE TO RELATED APPLICATIONS

This application claims the benefit of U.S. Provisional Application Ser. No. 63/025,436, filed on May 15, 2020, and U.S. Provisional Application Ser. No. 63/025,604, filed on May 15, 2020. The entire disclosures of the above applications are incorporated herein by reference.

FIELD

The present disclosure relates to augmented reality applications and, more particularly, medical applications employing augmented reality.

INTRODUCTION

This section provides background information related to the present disclosure which is not necessarily prior art.

Image-guided surgery has become standard practice for many different procedures. Image-guided surgery can visually correlate intraoperative data with preoperative data to aid a practitioner. The use of image-guided surgeries has been shown to increase the safety and the success of these procedures. Image-guided surgeries can be further enhanced through the use of augmented reality (AR) technology. AR is an interactive experience of a real-world environment where one or more features that reside in the real world are enhanced by computer-generated perceptual information, sometimes across multiple sensory modalities. In the medical settings, these AR technologies can be useful for enhancing the real environments in the patient care setting. For example, a practitioner can view content-specific information in the same field of view of the patient while performing a medical procedure, without having to change their gaze.

However, there are many difficulties that can arise during surgeries, even with current image-guided surgeries. For example, the anatomy of a patient is not necessarily static. Various internal movements, such as breathing or the heart beating, can cause a rhythmic shift in the internal anatomy of a patient. Undesirably, these internal movements may displace a surgical location, which can impair the use of augmented reality during the procedure. This problem can be further exacerbated by the fact that these internal motions are not linear. For example, inflation and deflation can result in significant changes in both lung deformation and volume of air flow as specific phases during the respiratory cycle.

What is more, one of the standard ways of producing a three-dimensional (3D) medical image today is through the use of a CT (computed tomography) scan which produces an image series which can be referred to as a DICOM data set. The DICOM data set can be further processed using software to segment out the structures of the body and to produce 3D images of these structures that can be used for further study or in the use of augmented reality. These DICOM data sets must be painstakingly looked at one at a time and then processed through a method of software segmentation, where each of the structures of interest within each individual scan slice must be outlined and identified.

Alternatively stated, the CT scans produce 2D (two dimensional) image slices of varying thickness. The individual 2D segmented DICOM slices then must be reassembled into a 3D model, rendered, and then smoothed. Processing the 2D image slices from the CT scans can include many image transfer and processing steps to produce an anatomical volume suitable to be viewed in augmented reality. Due to the numerosity of steps in this process, and the high cost to acquire and operate a CT scan, the viability of this scanning method can be unavailable for many people. Also, because of how costly CT scans can be, the number of available CT scans can be limited and not readily available to all patients in need. In addition, during a CT scan, it may be necessary for a patient to be exposed to a dose of radiation. This exposure to radiation can be harmful for human tissue which puts the patient and caregivers at risk. This radiation exposure may also result in longer term negative side effects.

Accordingly, there is a continuing need for a system and method for dynamic registration of anatomy using augmented reality. Desirably, the system and the method can adjust for various body movements.

SUMMARY

In concordance with the instant disclosure, a system and method for dynamic registration of anatomy using augmented reality, and which can adjust for internal body movements, has been surprisingly discovered.

The system and method can include an augmented reality environment, which can be fused with anatomical data and represented as at least one augmented representation. Desirably, a practitioner can use the augmented reality environment to confirm that positional gating of anatomical structures is accurate, and/or adjust augmented representations of active registrations. The computer system can provide translational, rotational, and/or deformation tools based on the desired refinement of the augmented representations of the active registrations. In addition, the system and method can employ closed loop feedback to alert the clinician of an optimal time to deliver therapy, execute a surgical procedure step to an anatomical feature, or relay pulses or time phased gated therapy delivery based on the augmented feedback. Rolling averages of spirometry data may also be used to refine animation of the augmented reality environment.

This technology can address the need for dynamic registration of human or animal anatomy using augmented reality or other digitally rendered visualization methods. During a surgery, robotic surgery, and/or minimally invasive surgery, the patient anatomy can move because of the respiratory cycle, cardiac cycle, and/or normal movement and physiological processes. The system and method can be applied to measure for movement of the body of the patient and gating that movement in the form of visualization feedback and/or animation.

In certain embodiments, systems for dynamic registration of autonomy using augmented reality can include an augmented reality system, an imaging system, a measuring system, and a computer system. The augmented reality system can be configured to display an augmented representation in an augmented reality environment. The imaging system can be configured to image an anatomical feature of the patient and can generate anatomical imaging data. The measuring system can be configured to measure an anatomical movement of the patient and can generate an anatomical movement data. The computer system can be in communication with the imaging system, the measuring system, and the augmented reality system. The computer system can be configured to receive the anatomical imaging and positional data from the imaging system and the anatomical movement data from the measuring system. The computer system can also be configured to generate the augmented representation based on the anatomical imaging data. In addition, the computer system can be configured to associate the augmented representation with the anatomical movement data. Also, the computer system can be configured to correlate the augmented representation with the anatomical movement data. The computer system can also be configured to render the augmented representation in the augmented reality environment on the augmented reality system. The computer system can be further configured to selectively update the augmented representation based on the anatomical movement data.

In certain embodiments, methods for dynamic registration of autonomy using augmented reality can include a step of providing the system for dynamic registration of anatomy using augmented reality. The system can include the imaging system, the measuring system, and the computer system. The imaging system can image the anatomical feature of the patient. The imaging system can generate the anatomical imaging data from imaging the anatomical feature of the patient. The measuring system can measure the anatomical movement of the patient. The measuring system can generate the anatomical movement data from measuring the anatomical movement of the patient. The computer system can receive the anatomical imaging data and the anatomical movement data. The computer system can generate the augmented representation based on the anatomical imaging data. The computer system can associate the augmented representation with the anatomical feature of the patient. The computer system can correlate the augmented representation with the anatomical movement data of the patient. The computer system can render the augmented representation in the augmented reality environment on the augmented reality system. The computer system can selectively update the augmented representation based on the anatomical movement data.

The system and method can allow for the following clinical advantages: i) improve adoption of surgical mixed reality guidance and navigation by militating against the requirement for costly CT scanning devices; ii) reduce procedure time by reducing many image transfer and processing steps to produce an anatomical volume viewed in augmented reality; iii) reduce the need of harmful radiation to patient and caregivers; and iv) improve imaging capabilities of non-static anatomical structures.

It should be appreciated that while the present disclosure is primarily directed to augmented reality (AR) technology and the associated applications, the present disclosure can also be applied to virtual reality (VR) technology and the associated applications, including mixed reality (MR) applications.

Further areas of applicability will become apparent from the description provided herein. It should be understood that the description and specific examples are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
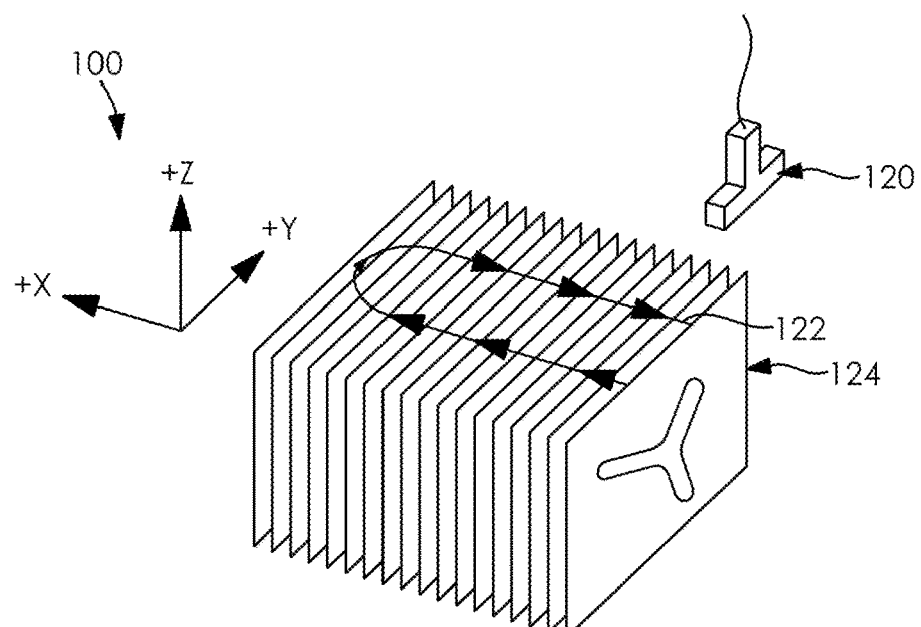
Figure 3:
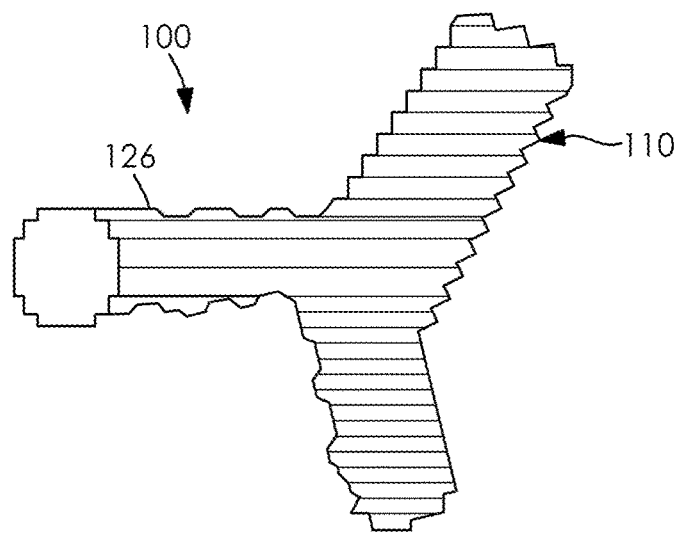

FIG. 1 is a schematic view of a system, according to certain embodiments, showing an augmented reality system, an imaging system, a measuring system, and a computer system;

FIG. 2 schematically depicts the system in operation, according to certain embodiments, and further showing a process of obtaining 2D images, which can be incorporated into at least one of imaging and positional data and anatomical movement data by moving an ultrasound probe over an anatomical feature of the patient and pausing for a predetermined time at a set pause interval;

FIG. 3 schematically depicts an augmented representation of the anatomical feature, which can be generated by the computer system using the imaging and positional data, according to certain embodiments, and having jagged edges that can result from the generation process.

Figure 4:
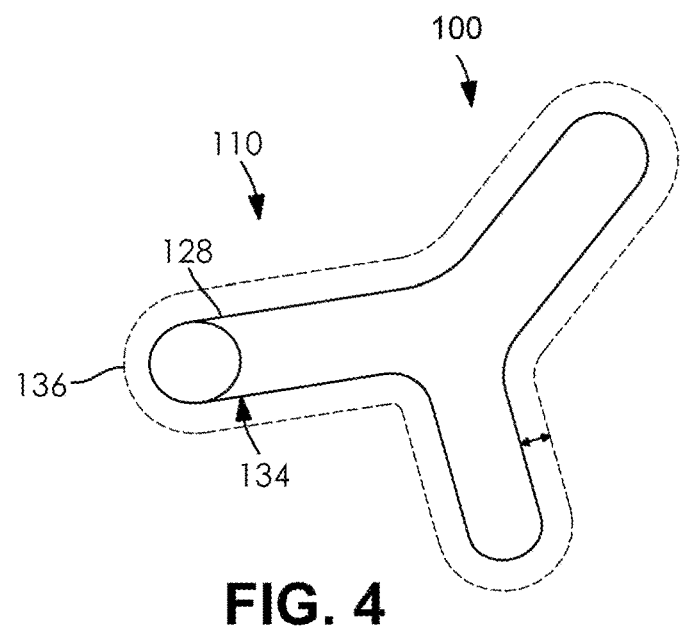
Figure 5:
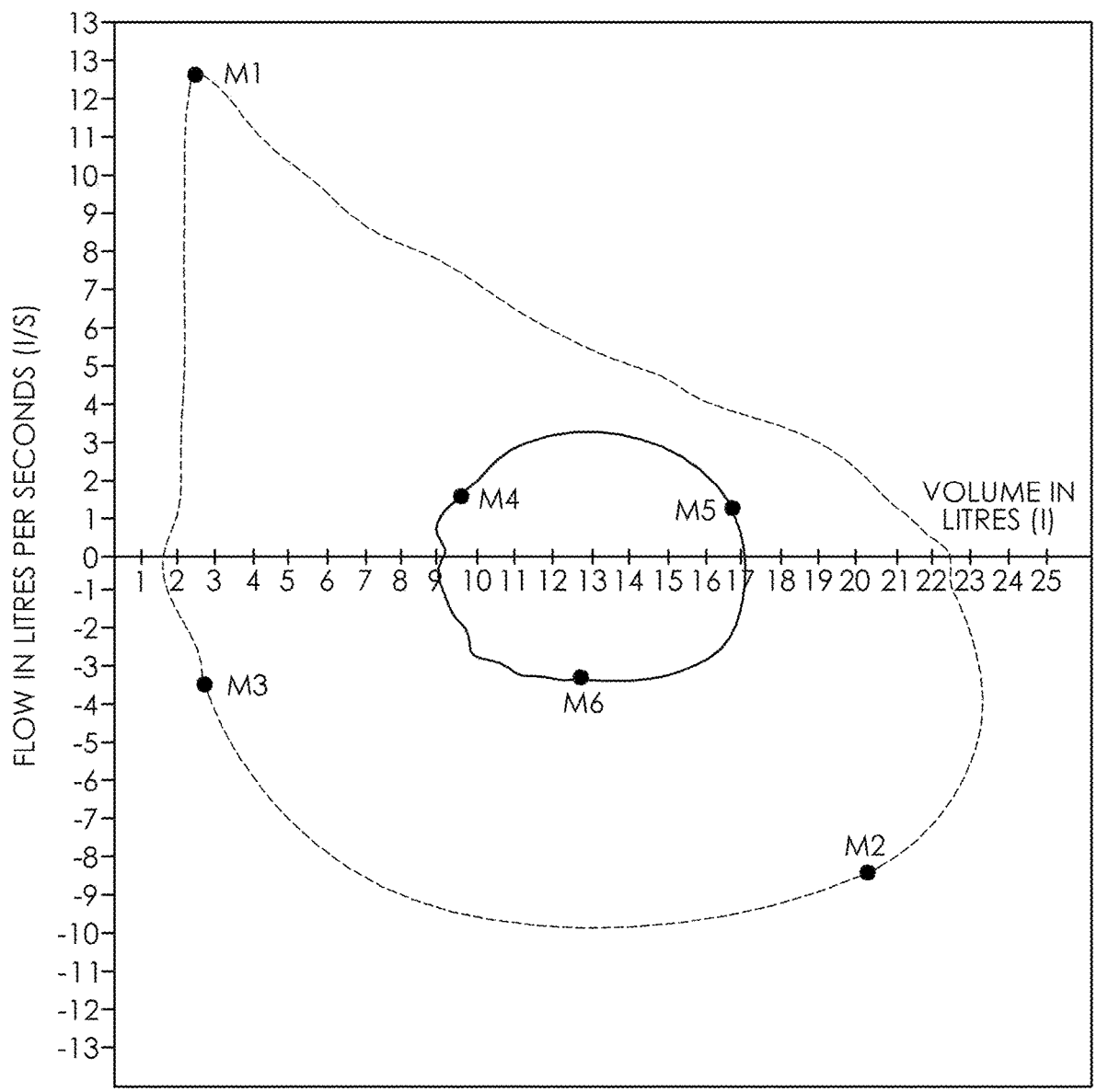
Figure 6:
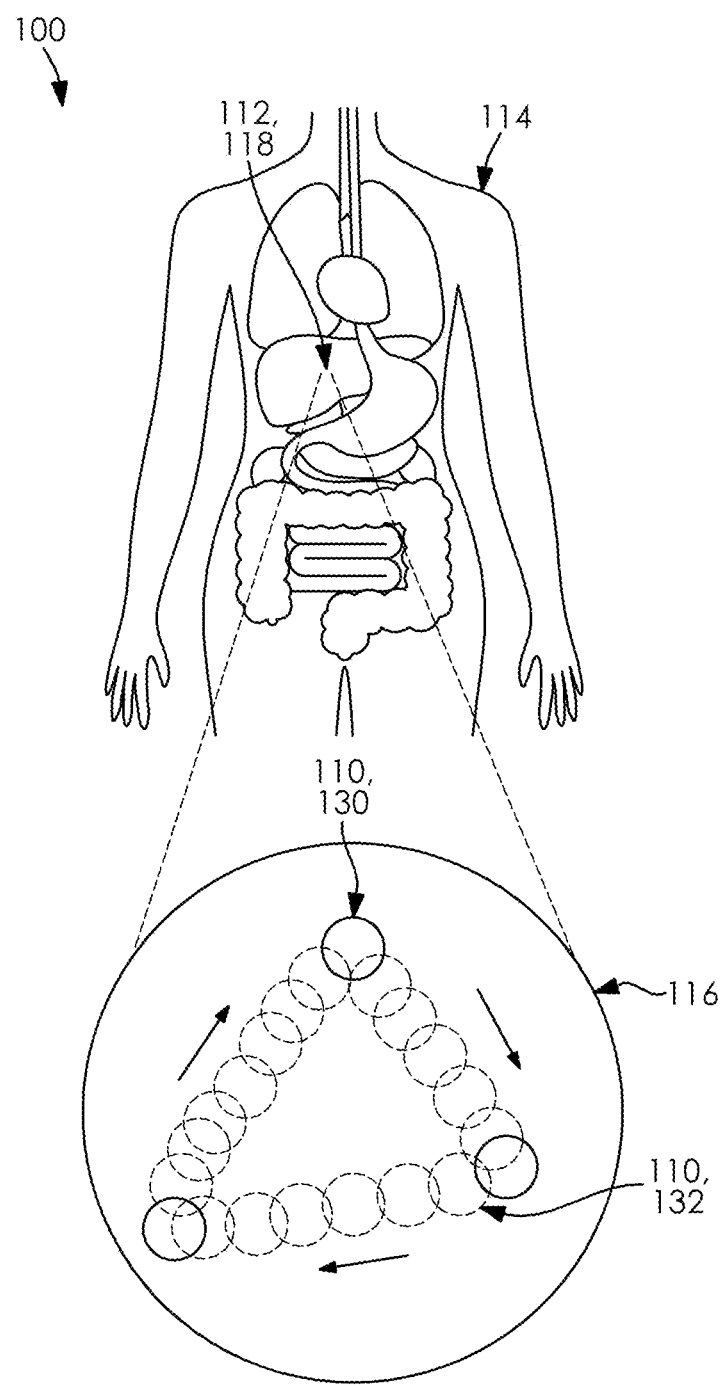
Figure 7:
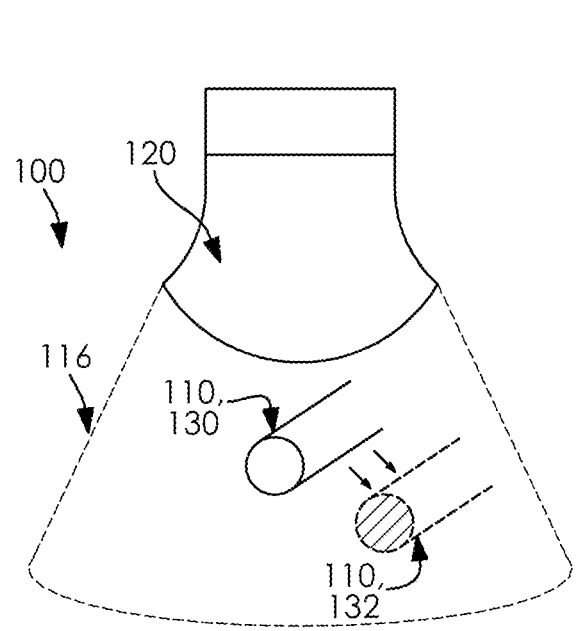
Figure 8:
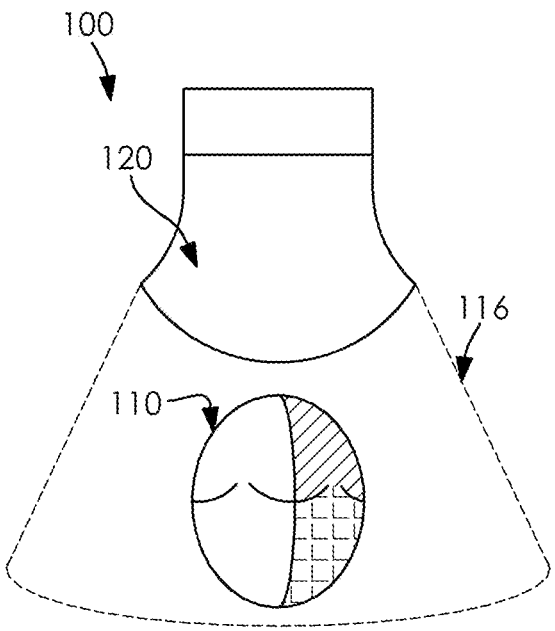
Figure 9:
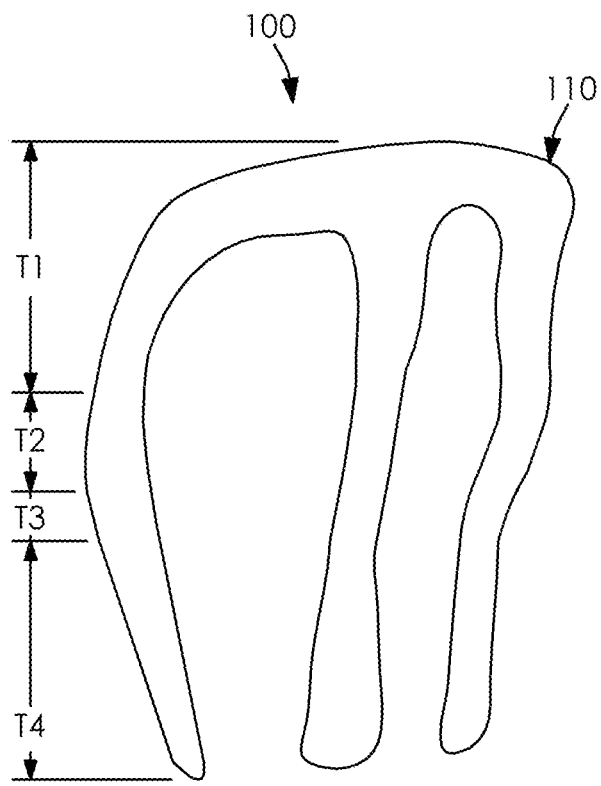
Figure 9:
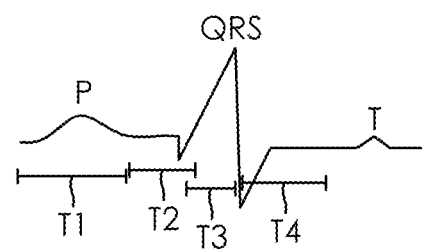
Figure 10A:
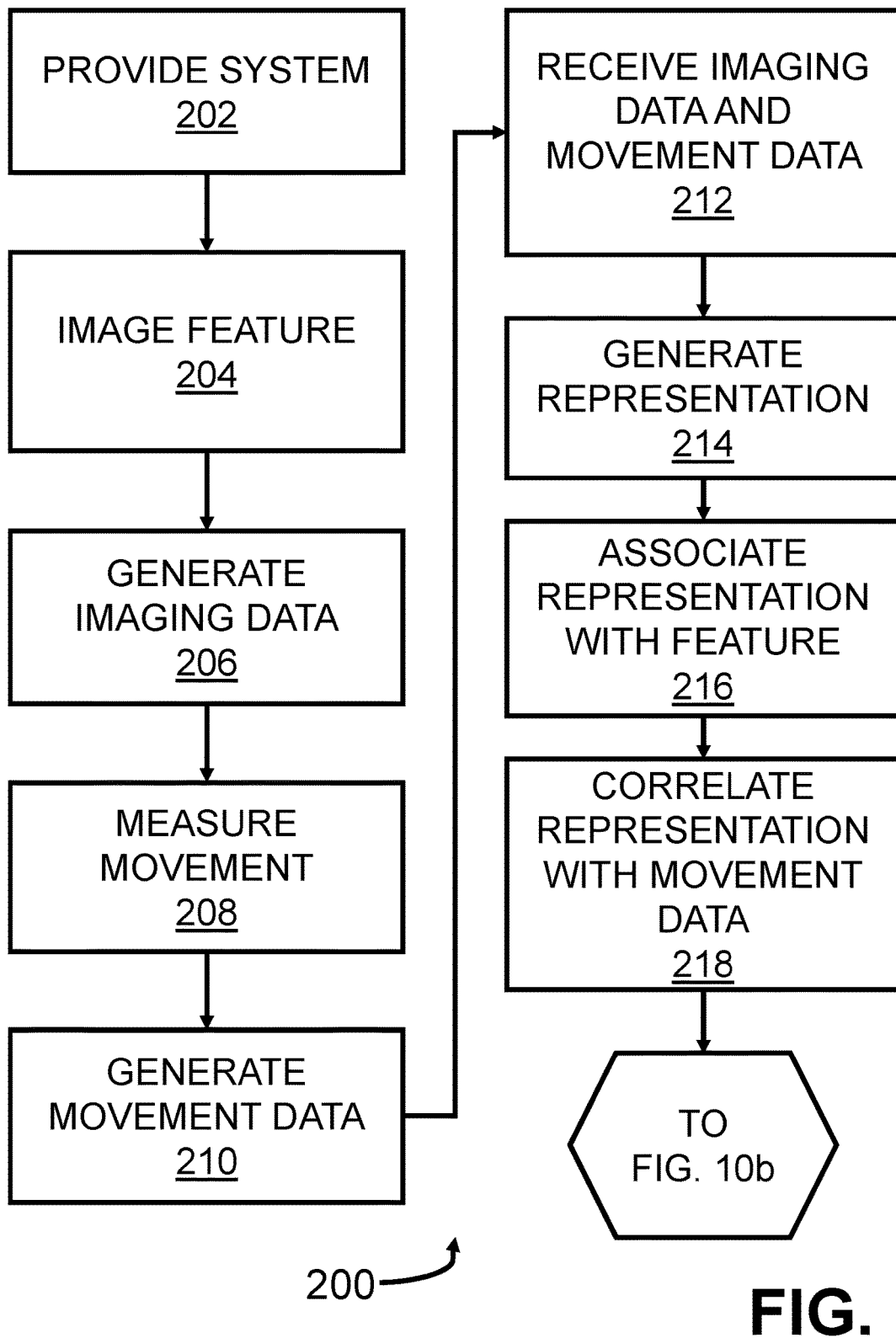
Figure 10B:
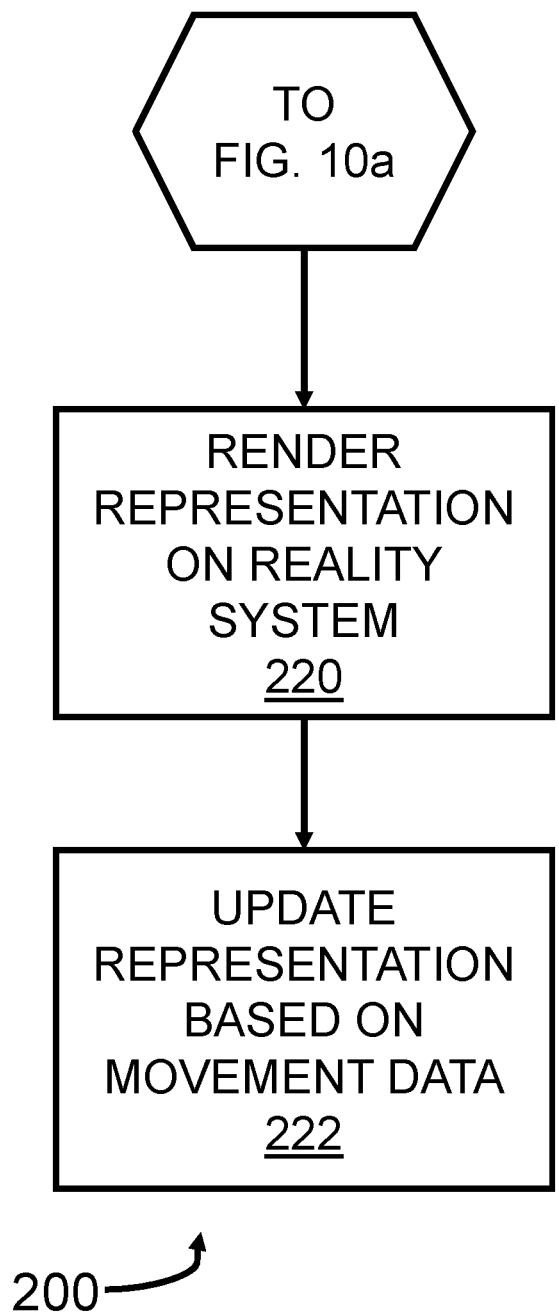
Figure 11A:
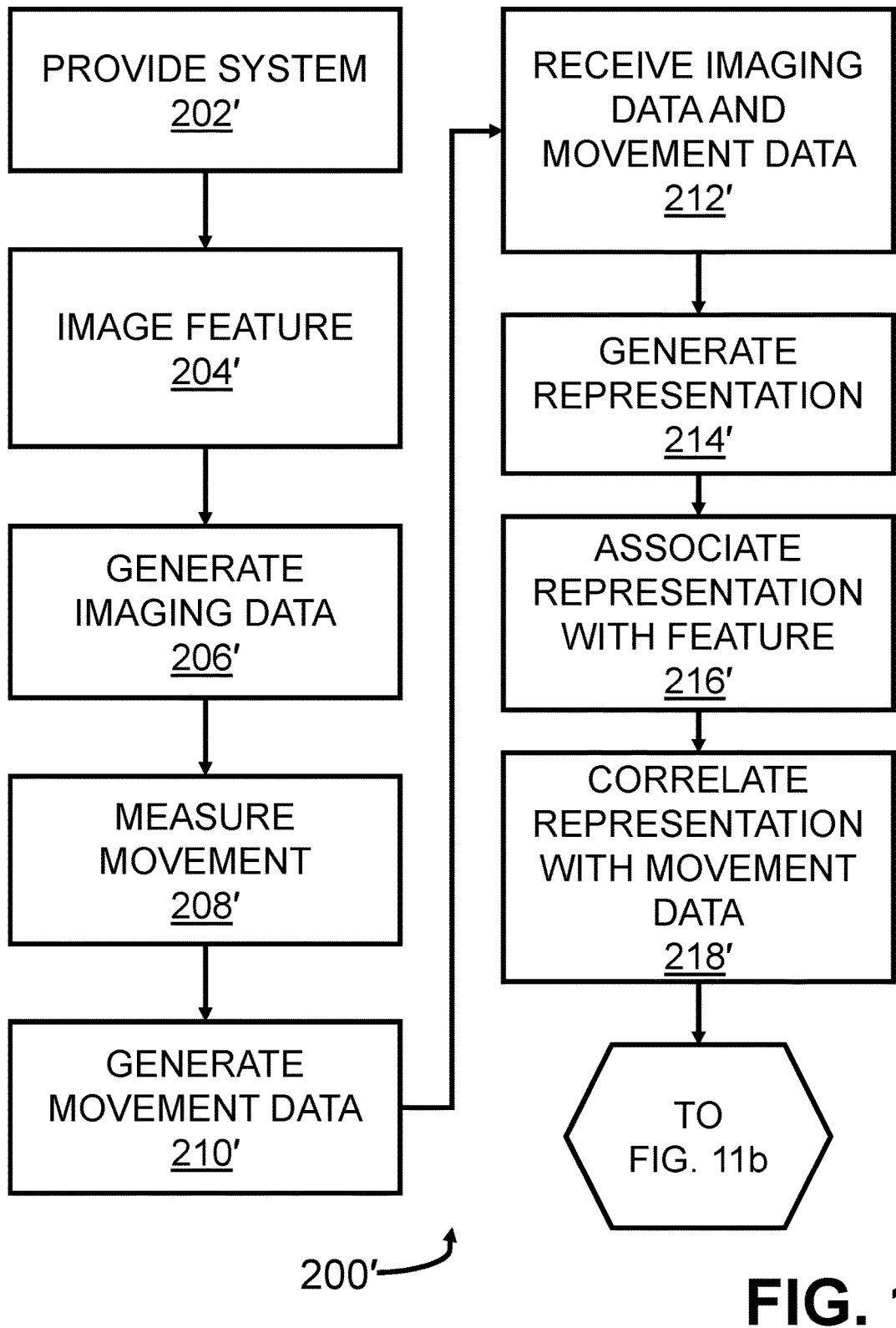
Figure 11B:
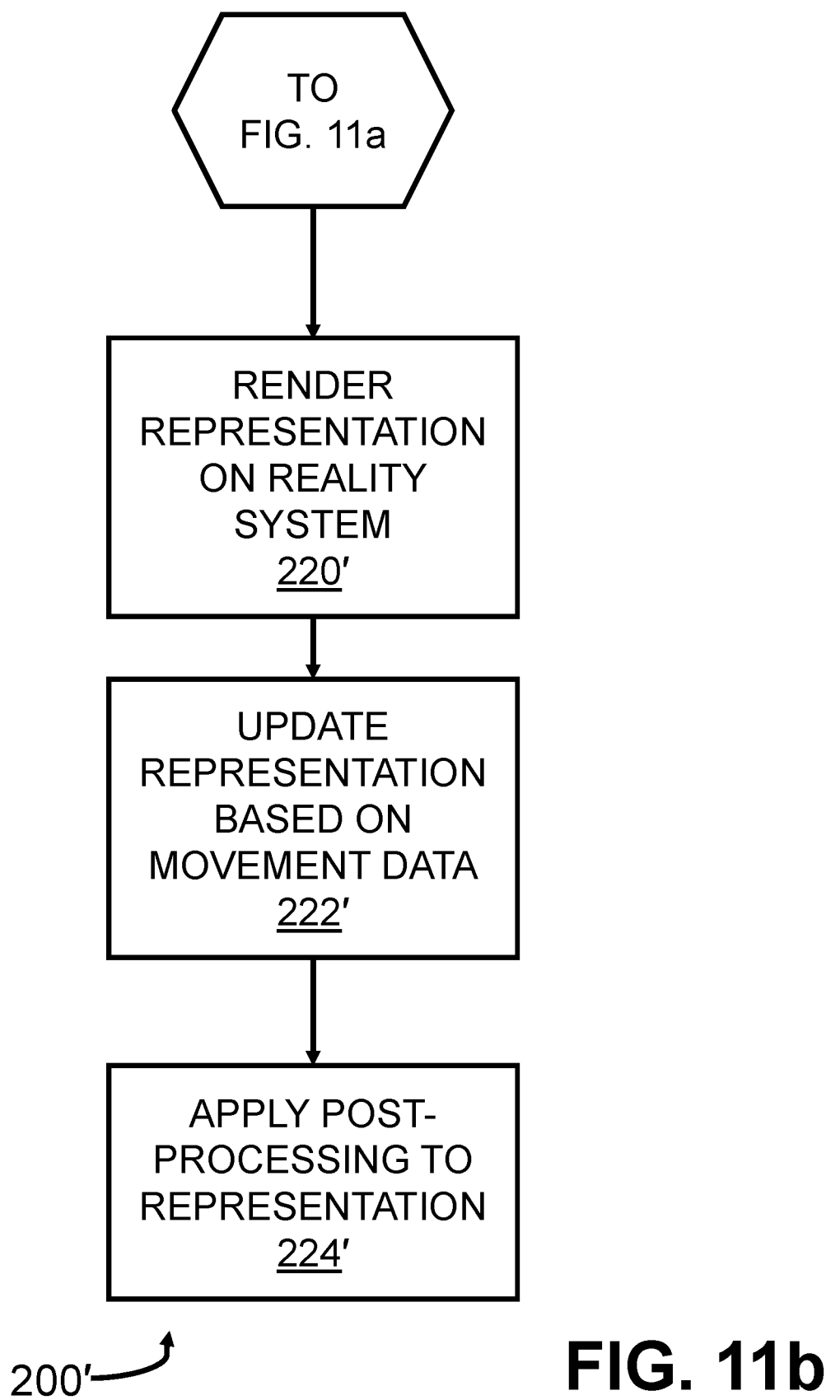

FIG. 4 schematically depicts the augmented representation shown in FIG. 3 with the jagged edges smoothed out using post-processing, and further showing a phantom outline that designates a boundary that the augmented representation can expand to, which can reflect how the anatomical feature expands based on an anatomical movement;

FIG. 5 graphically depicts spirometry data having a plurality of reference points, which can be incorporated into the anatomical movement data, according to certain embodiments, and can be used by the computer system determine how to update the augmented representation;

FIG. 6 schematically depicts the system in operation, according to certain embodiments, showing an augmented reality environment having the augmented representation rendered over a portion of the patient, and further showing a position of the augmented representation changing, reflecting how the anatomical feature moves based on the anatomical movement;

FIG. 7 schematically depicts the system in operation, according to certain embodiments, showing the augmented reality environment being displayed using a flashlight display method, and further showing the augmented representation shifting position based on the anatomical movement;

FIG. 8 schematically depicts the system in operation, according to certain embodiments, showing the augmented reality environment being displayed using a flashlight display method, and further showing the augmented representation including an area representing where blood is flowing towards the ultrasound probe (shown as a stripe pattern) in the anatomical feature and an area depicting where the blood if flowing away from the ultrasound probe (show as a square pattern) in the anatomical feature;

FIG. 9 schematically depicts the augmented representation, according to certain embodiments, and further showing an ECG waveform with designated segments that can be used to determine a minimum and a maximum range of movement of the augmented representation, according to how the anatomical feature can move during a cardiac cycle of the patient;

FIGS. 10a and 10b are flowcharts illustrating a method for using the system, according to certain embodiments; and FIGS. 11a and 11b are flowcharts illustrating a method for using the system, according to certain embodiments; and further showing a step of applying post-processing to the augmented representation.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the FIGS. is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

All documents, including patents, patent applications, and scientific literature cited in this detailed description are incorporated herein by reference, unless otherwise expressly indicated. Where any conflict or ambiguity can exist between a document incorporated by reference and this detailed description, the present detailed description controls.

As used herein, the term "head-mounted device" or "headset" or "HMD" refers to a display device, configured to be worn on the head, that has one or more display optics (including lenses) in front of one or more eyes. These terms may be referred to even more generally by the term "augmented reality system." An example of a suitable head-mounted device is a Microsoft HoloLens®.

FIG. 1 illustrates a system for dynamic registration of anatomy using augmented reality 100. The system 100 can have an augmented reality system 102, an imaging system 104, a measuring system 106, and a computer system 108. The augmented reality system 102 can be configured to display an augmented representation 110, as shown in FIGS. 3-4 and 6-9. The augmented representation 110 can be a two-dimensional (2D) or a three-dimensional (3D) depiction of relevant information to the current medical procedure. Non-limiting examples of the relevant information can include preoperative and/or intraoperative data, such as three-dimensional depictions of an anatomical feature 112 of a patient 114. The anatomical feature 112 can be the organic matter and/or region of the patient 114 that is the focus of the current procedure. Further non-limiting examples of the anatomical feature 112 can include organs, portions of organs, tissues, joints, bones, tumors, implants, etc. The augmented representation 110 can have many applications and uses such as pre-procedural planning, procedural guidance, and training. It should be appreciated that one skilled in the art can select other information to be depicted for the augmented representation 110. In addition, it should be appreciated that the anatomical feature 112 can include any portion of the anatomy of the patient 114.

While still referring to FIGS. 3-4 and 6-9, the augmented reality system 102 can be configured to display the augmented representation 110 in an augmented reality environment 116. The augmented reality environment 116 can include a virtual window and/or different modes, such as the "head-up-display" or "HUD" mode, shown in FIGS. 3-4, 6, and 9, and the "flashlight" mode, shown in FIGS. 7-8, and as described in U.S. application Ser. No. 17/110,991 to Black et al., the entire disclosure of which including definitions are incorporated herein by reference. Desirably, this can allow a practitioner to view the augmented representation 110 in the same field of view of the patient 114. Now referencing to FIG. 6, the augmented reality system 102 can be configured to display an augmented representation 110 over a portion 118 of the patient 114 in an augmented reality environment 116. In certain examples, the portion 118 of the patient 114 can be the anatomical feature 112 of the patient 114. Advantageously, this can allow the augmented representation 110 to be depicted directly over the anatomical feature 112 to provide relevant feedback within the context of a position of the anatomical feature 112. For example, the augmented representation 110 can be an intraoperative scan of the anatomical feature 112 that can be overlaid over the anatomical feature 112 to the practitioner. In other instances, the portion 118 of the patient 114 can be adjacent to the anatomical feature 112 of the patient 114. Desirably, this can permit the practitioner to observe the augmented representation 110, while also being able to observe the anatomical feature 112, within the same field of view; e.g., a mixed reality view.

In certain examples, the augmented representation 110, using the augment reality display, can be displayed over an approximated position of the anatomical feature 112 of the patient 114. For example, the computer system 108 can employ algorithms, machine learning, artificial intelligence, and/or in combination to approximate where the anatomical feature 112 of the patient 114 is according to medically approved tolerances. However, it should be appreciated that the augmented representation 110 can also be displayed on other surfaces and/or augmented representations, as desired.

The augmented reality system 102 can be a headset display, which can be worn by a user. A non-limiting example of the augmented reality system 102 can be the Microsoft HoloLens®. The augmented reality system 102 and the method of operation, including the method of displaying the augmented representation 110 can include those described in U.S. Pat. No. 10,478,255 to West et al.; U.S. Pat. No. 10,895,906 to West et al.; U.S. Pat. No. 10,869,727 to Yanof et al.; U.S. Patent Pub. No. 2021/0081035 to West et al.; U.S. patent application Ser. No. 17/117,841 to Martin et al.; U.S. patent application Ser. No. 17/213,636 to Black et al.; U.S. patent application Ser. No. 17/163,975 to Black et al.; and U.S. application Ser. No. 17/110,991 to Black et al., the entire disclosures of which including definitions are incorporated herein by reference. However, it should be appreciated that a skilled artisan can employ other AR devices and methods of operation for the augmented reality system 102, within the scope of this disclosure.

It should be appreciated that in certain embodiments the augmented reality system 102 can also include one or more positional sensors 138. The positional sensors 138 of the augmented reality system 102 can be configured to determine and generate positional data 140 for the augmented reality system 102, such as the approximated position in three-dimensional (3D) space, the orientation, angular velocity, and acceleration of the augmented reality system 102. For example, it should be understood that this can allow holographic imagery to be accurately displayed within the field of view of the practitioner, in operation. Non-limiting examples of the positional sensors 138 include accelerometers, gyroscopes, electromagnetic sensors, and/or optical tracking sensors. It should further be appreciated that a skilled artisan can employ different types and numbers of positional sensors 138 of the augmented reality system 102, for example, as required by the procedure or situation within which the augmented reality system 102 is being used.

The imaging system 104 can be configured to image the anatomical feature 112 of the patient 114 and generate anatomical imaging data 142. The anatomical imaging data 142 can include information and/or media associated with the structure, rotation, and/or position of the anatomical feature 112 in relation to the patient 114. It should be appreciated that one skilled in the art can select types of data to be included in the anatomical imaging data 142. Desirably, the imaging system 104 can be utilized to image the anatomical feature 112 of the patient 114 and generate the anatomical imaging data 142 before a procedure, during a procedure, and/or in combination.

As will be described in further detail below, the anatomical imaging data 142 can be utilized by the computer system 108 to generate the augmented representation 110. In other words, the imaging system 104 can be used to perform a scan and/or other imaging procedure to generate the anatomical imaging data 142 to be used to generate the augmented representation 110. For example, the imaging system 104 can include an ultrasound system having at least one ultrasound probe 120. The practitioner can move the ultrasound probe 120 over the anatomical feature 112 of the patient 114 to capture the anatomical imaging data 142, which can include 2D images 124. FIG. 2 illustrates the ultrasound system, as the imaging system 104, with the ultrasound probe 120. The ultrasound probe 120 can be moved along a path 122 along the patient 114 to generate the 2D images 124. The 2D images 124 can then be transformed by the computer system 108 into the augmented representation 110. Other non-limiting examples of the imaging system 104 can include computed tomography (CT) systems, electromagnetic systems, cone beam computed tomography (or CBCT) systems, blood gas exchange systems, mechanically controlled ventilation systems, spirometry systems, electrocardiogram (ECG) systems, magnetic resonance imaging (MRI) systems, electromechanical wave propagation systems, transesophageal echocardiogram (TEE) systems, and combinations thereof. However, it should be appreciated that a skilled artisan can employ other imaging procedures and systems for the imaging system 104, within the scope of this disclosure.

The measuring system 106 can be configured to measure an anatomical movement of the patient 114 and generate an anatomical movement data 144. The anatomical movement can include one or more movements in one or more portions of the body of the patient 114 that can occur based a partial or complete movement cycle of the patient 114. Non-limiting examples of the movement cycle can include external forces or internal forces, such as movements based on the respiratory cycle, cardiac cycle, movement of a joint including a range of motion of joint, internal anatomies shifting, and/or physiologic processes. Other movement cycles that can affect the anatomical feature of the patient can also be measured, within the scope of this disclosure. In addition, the anatomical movement can include multiple cycles of the movement. The anatomical movement can influence several aspects of the anatomical feature 112, such as the structure, position, rotation, etc, which can be captured in the anatomical movement data.

The anatomical movement data 144 can include information and/or media associated with the anatomical movement and the effects the anatomical movement has on the anatomical feature 112. In certain examples, the anatomical movement data 144 can include displacement and strain measurements, which can be used to delineate and visually show areas of diseased or sclerotic tissue for optimal implant and implant repair procedures. It should be appreciated that a person skilled in the art can select other data and information to be included in the anatomical movement data, as desired.

As will be described in further detail below, the anatomical movement data 144 can be utilized by the computer system 108 to update the augmented representation 110 based on the anatomical movement data. This can allow aspects of the augmented representation 110 to selectively update based on the internal movement. Desirably, the augmented representation 110 can remain useable regardless of internal movement in the body of the patient 114. The measuring system 106 can be utilized to measure the anatomical movement of the patient 114 and generate the anatomical movement data 144 before a procedure, during a procedure, and/or in combination. The measuring system 106 can be configured to permit gating the anatomical movement of patient 114 and generate the anatomical movement data. With reference to FIG. 5, the measuring system 106 can include a spirometry system to measure the anatomical movement associated with respiration and generate the anatomical movement data. Other non-limiting examples of the measuring system 106 can include computed tomography (CT) systems, electromagnetic systems, cone beam computed tomography (or CBCT) systems, blood gas exchange systems, mechanically controlled ventilation systems, spirometry systems, electrocardiogram (ECG) systems, magnetic resonance imaging (MRI) systems, electromechanical wave propagation systems, transesophageal echocardiogram (TEE) systems, and combinations thereof. It should be appreciated that one skilled in the art can employ other systems for the measuring system 106, as desired.

It should be appreciated that a skilled artisan can combine the imaging system 104 and the measuring system 106 into a single system and/or add on or more additional systems, within the scope of the disclosure. Likewise, the anatomical imaging data 142 and the anatomical movement data 144 can be combined into a single data entry and/or additional data entries, as desired. In addition, further examples of the imaging system 104 and the measuring system 106, as well as methods of operation will be described in further details below.

Now referring to FIG. 1, the computer system 108 can be in communication with the augmented reality system 102, the imaging system 104, and/or the measuring system 106. This can be accomplished via wireless connections, wired connections, or through a network 152. It should be appreciated that the network 152 of the system 100 can include various wireless and wired communication networks, including a radio access network, such as LTE or 5G, a local area network (LAN), a wide area network (WAN) such as the Internet, or wireless LAN (WLAN), as non-limiting examples. It will be appreciated that such network examples are not intended to be limiting, and that the scope of this disclosure includes implementations in which one or more computing platforms of the system 100 can be operatively linked via some other communication coupling, including combinations of wireless and wired communication networks. One or more components and subcomponents of the system 100 can be configured to communicate with the networked environment via wireless or wired connections. In certain embodiments, one or more computing platforms can be configured to communicate directly with each other via wireless or wired connections. Examples of various computing platforms and networked devices include, but are not limited to, smartphones, wearable devices, tablets, laptop computers, desktop computers, Internet of Things (IoT) devices, or other mobile or stationary devices such as standalone servers, networked servers, or an array of servers.

The computer system 108 can have a processor 146 and a memory 148. The memory 148 can include non-transitory processor-executable instructions 150 to perform several different operations. For example, the computer system 108 can be configured to receive the anatomical imaging data 142 from the imaging system 104 and the anatomical movement data 144 from the measuring system 106. In addition, as mentioned previously, the imaging system 104 and the measuring system 106 can be a single system and/or additional or separate systems. Thus, the computer system 108 can receive the anatomical imaging data 142 and the anatomical movement data 144 from a single system and/or multiple systems.

The computer system 108 can be also configured to generate the augmented representation 110 based on the anatomical imaging data 142. This may be accomplished via inputs from the user, algorithms, machine learning, artificial intelligence, and/or in combination. In certain examples, the computer system 108 can generate the augmented representation 110 based on the systems and methods, as described in U.S. Pat. No. 10,478,255 to West et al. and/or U.S. Pat. No. 10,895,906 to West et al.

With reference to FIGS. 3-4, the computer system 108 can be configured to apply post-processing effects to enhance the augmented representation 110. For example, the computer can apply anti-aliasing to the augmented representation 110 to smooth out jagged edges 126 into smoothed edges 128 that can be formed during the generation process. This can be accomplished using a multitude of different anti-aliasing technologies and techniques. Non-limiting examples can include Supersample Anti-Aliasing (SSAA), Multi-Sampling Anti-Aliasing (MSAA), Fast Approximate Anti-Aliasing (FXAA), Temporal Anti-Aliasing (TXAA), etc. The smoothing can also include operations as simple as averaging and estimating data between measuring points; e.g., the smoothing of noise between data sets and/or estimating and filling in gaps between data points. The computer system 108 can also employ algorithms, machine learning, artificial intelligence, individually or in combination to apply the anti-aliasing. Advantageously, this can permit the augmented representation 110 to appear clearer to the practitioner as well as provide an optimization of a location, size, position, orientation, and/or animation of the augmented representation 110. It should be appreciated that one skilled in the art can employ other processes and methods for smoothing the jagged edges 126 into the smoothed edges 128 of the augmented representation 110.

The computer system 108 can also be configured to associate the augmented representation 110 with the anatomical feature 112 of the patient 114. In certain examples, this can be achieved by integrating the augmented representation 110 into a holographic registration relative to the patient 114, as described in U.S. Pat. No. 10,478,255 to West et al. and/or U.S. Pat. No. 10,895,906 to West et al. Desirably, associating the augmented representation 110 with the anatomical feature 112 of the patient 114 permits anatomical imaging and positional data to be put into a common holographic coordinate system utilized by the augmented reality system 102 to provide the augmented reality environment 116 with the augmented representation 110. However, it should be appreciated that a skilled artisan can employ different methods for associating the augmented representation 110 with the anatomical feature 112 of the patient 114, as desired.

The computer system 108 can be further configured to correlate the augmented representation 110 with the anatomical movement data. In other words, the computer system 108 can determine the relationship between the augmented representation 110 and the anatomical movement data, which can determine if the augmented representation 110 needs to be updated according to the anatomical movement of the patient 114. This can also be accomplished using a variety of algorithms, machine learning, and artificial intelligence. In addition, certain applications will be discussed below to further explain how the correlation can occur between the augmented representation 110 and the anatomical movement data 144.

With reference to FIGS. 3-4, 6-9, the computer system 108 can also be configured to render the augmented representation 110 on in the augmented reality environment 116 on the augmented reality system 102. In certain examples, the computer system 108 can be configured to render the augmented representation 110 over the portion 118 of the patient 114 in the augmented reality environment 116 on the augmented reality system 102, as shown in FIG. 6. As mentioned previously, this can allow the practitioner to view the augmented representation 110 in the augmented reality environment 116 within the same field of view as the patient 114. In certain examples, the augmented representation 110 can be associated with an implant, instrument, and/or tool for optimal deployment and/or utilization, like shown in FIGS. 7-8.

Now referring to FIGS. 4, 6, and 7, the computer system 108 can be further configured to selectively update the augmented representation 110 based on the anatomical movement data 144. In certain examples, updating the augmented representation 110 can include updating a position of the augmented representation 110 in the augmented reality environment 116 according to the anatomical movement data 144. As non-limiting examples, FIGS. 6 and 7 show the augmented representation 110 being updated to change the position of the augmented representation 110 according to the anatomical movement data 144 (an original position 130 being shown in solid lines and an updated position 132 being shown in dashed lines). Desirably, the updated position 132 of the augmented representation 110 can reflect how the position of the anatomical feature 112 changed because of the anatomical movement of the patient 114. For example, a cancerous lesion in a liver of the patient 114 can experience a change in position based on the respiratory cycle of the patient 114. Thus, the computer system 108 can compensate for the position of the anatomical feature 112 changing because of the anatomical movement of the patient 114. Advantageously, this can allow the augmented representation 110 to remain useful, even if the position of the anatomical feature 112 changes because of the anatomical movement.

With reference to FIG. 4, updating the augmented representation 110 can include animating the augmented representation 110 based on the anatomical movement data 144, thereby showing structural changes of the augmented representation 110. For example, a structure of the augmented representation 110 can be animated to expand, contract, deform, or reform according to the anatomical movement data 144. As a non-limiting example, FIG. 4 depicts the augmented representation 110 being updated to expand according to the anatomical movement data 144 (an original state 134 being shown in solid lines and a boundary 136 where the feature will expand to being shown in dashed lines). Desirably, this can allow the practitioner to visually see the augmented representation 110 expanding to the boundary 136, which reflects how the anatomical feature 112 changed because of the anatomical movement. It is believed that this can aid in a procedure where current state of the anatomical feature 112 based on the anatomical movement is relevant to the practitioner.

In other examples, updating the augmented representation 110 can include updating the position and/or structure of the augmented representation 110 according to the anatomical movement data 144, without showing the animation of the transition. Desirably, this can save on processing power where showing the transition is not necessary.

The computer system 108 can be configured to selectively update the augmented representation 110 based on the anatomical movement data 144 at a set update interval. The update interval can be scaled according to the requirements of the current medical procedure. For example, if the procedure needs more accuracy, the update interval can be shorter to allow the update to occur more frequently. If the procedure does not require as much accuracy, the update interval can be longer to occur less frequently. In certain examples, the augmented representation 110 can be updated nearly continuously based on the anatomical movement data 144. However, it should be appreciated that a skilled artisan can scale the update interval according to the requirements of the procedure.

It should be appreciated the computer system 108 can selectively update the augmented representation 110 automatically based on the anatomical movement data 144. However, in certain examples, the computer system 108 can be configured to permit the practitioner to decide when the augmented representation 110 is updated. For example, an input can be provided to the system by the practitioner or another individual in order to effect a manual update of the augmented representation 110, as desired.

In addition, the computer system 108 can be adapted to various levels of computing power by using rolling averages to predict motion within a certain confidence interval thus relieving the computer processing burden required for a clinically acceptable level of performance. It should be appreciated that in some instances, the computer system 108 can be external to the augmented reality system 102. However, in some instances, the computer system 108 can be contained with the augmented reality system 102.

The system 100 can further include tracking sensors may be employed to aid in imaging the anatomical imaging data 142 and measuring the anatomical movement data 144. For example, the tracking sensors can include an electromagnetic system to track instruments, such as the ultrasound probe 120, and generate tracking data that can be incorporated into the anatomical image and positional data and the anatomical movement data 144. Tracking data can also include the approximated position in 3D space, the orientation, angular velocity, and acceleration of tracked instruments. Non-limiting examples of the tracking sensors can include accelerometers, gyroscopes, electromagnetic sensors, and optical tracking sensors. However, it should be appreciated that a skilled artisan can employ different devices and instruments for the tracking sensors, within the scope of this disclosure.

Respiration Application

As shown in FIGS. 5-6, the measuring system 106 can be configured to measure the anatomical movement occurring from respiration and generate the anatomical movement data 144. For example, the measuring system 106 can include a spirometry system, a blood gas exchange system, and/or a mechanically controlled ventilation system to measure the anatomical movement, relating to respiration, and generate the anatomical movement data 144. Other technology, such as the CT systems, the MRI systems, the ultrasound systems, and the ECG systems can also be employed to capture the anatomical movement and generate and/or supplement the anatomical movement data 144.

Typical respiration can average around 5-7 mg/kg of body weight, however inflation and deflation of the lungs is not linear. Inflation and deflation can have significant changes in both lung deformation and volume of air flow as specific phases during the respiratory cycle. The imaging system 104 can include performing spirometry measurements, which can include taking measurements of a volume of air over a seven (7) breath average.

The measuring system 106 can capture the real time spirometry data using wireless spirometry or mechanical ventilation in relation to the targeted area of surgical intervention. One surgical intervention example includes a cancerous lesion in the liver. The cancerous lesion can experience change in position based on the respiratory cycle. This change of position can be captured by the measuring system 106 and generated into anatomical movement data 144. Then, the computer system 108 can selectively update the augmented representation 110 by showing animation or visual feedback to the practitioner. The position of the cancerous lesion can be captured in relation to a known phase in the respiratory cycle demonstrating a time point (respiratory cycle) by the measuring system 106. The computer system 108 can correlate the position of the cancerous lesion and with a known volume of air in the lungs of the patient 114 associated with the time point. The measuring system 106 can then capture and/or refine the anatomical movement data 144 using real time 2D, 3D, 4D ultrasound to capture the position of the anatomical feature 112, such as the cancerous lesion. Other systems and methods can also be employed by a skilled artisan, within the scope of this disclosure.

The computer system 108 can apply the anatomical movement data 144 to X,Y,Z coordinates at differing time points demonstrating the gating and deformation of the anatomical feature 112. The measuring system 106 can include ultrasound systems, MRI systems, or CT systems, which can generate anatomical movement data 144, such as the elastography characteristics of the anatomical feature 112. The computer system 108 can use the anatomical movement data 144 to provide dynamic deformation of the augmented representation 110, which reflects the how the movement affected the anatomical feature 112.

In certain examples, the measuring system 106 can measure the anatomical movement of the patient 114 that can occur when the patient inhales and/or exhales. Based on these measurements, the measuring system 106 can include spirometry data, which can be incorporated into the anatomical movement data 144. The measuring system 106 can include a spirometer and/or a bellows type device to accomplish measuring and generating the spirometry data. However, it should be appreciated that a skilled artisan can employ different systems and methods to collect the spirometry data for the measuring system 106. The spirometry data can include a flow volume loop to create reference points in the respiratory cycle of the patient 114. In particular, FIG. 6 shows a graph of the spirometry data having a first measurement (M1), a second measurement (M2), a third measurement (M3), a fourth measurement (M4), a fifth measurement (M5), and a sixth measurement (M6). These measurements, M1, M2, M3, M4, M5, and/or M6, can be used to correlate the position of the augmented representation 110 with a known volume of air in the lungs of the patient 114 associated with a particular time point. The computer system 108 can then update the augmented representation 110 according to the spirometry data. For example, the computer system 108 can update the position of the augmented representation 110 to reflect how the position of the anatomical feature 112 moves due to the inhaling and/or exhaling, as well a complete respiration cycle or over multiple cycles. This can be particularly useful for when the anatomical feature 112 includes a tumor, cyst, blood vessel, heart structure, muscle, bone, and/or nerve.

Cardiac Cycle Application

During structural heart repair or replacement procedures and electrophysiology ablation procedures, methods can be applied using diagnostic imaging correlated to cardiac cycle or cardiac pacing. Using diagnostic imaging such as the CT systems, the MRI systems, TEE systems, ECG systems, and/or electromechanical wave propagation systems, similar solutions can be achieved. However, it should be appreciated that a skilled artisan can employ other different types of diagnostic and measurement systems for the imaging system 104 and the measuring system 106, as desired. During the cardiac cycle, using the measuring system 106 can include known cardiac output (Q) or pacing characteristic, the amount of cardiac motion can be visualized using gating techniques.

In certain examples, the measuring system 106 can include an ECG system. The ECG system can generate ECG data, including an ECG electrical cycle, and relate the ECG data to the mechanical cycle of the heart, which can be incorporated into the anatomical movement data 144. The ECG electrical cycle can have three main components: the P wave, which represents the depolarization of the atria; the QRS complex, which represents the depolarization of the ventricles; and the T wave, which represents the repolarization of the ventricles. With reference to FIG. 9, the computer system 108 can update the augmented representation 110 according to the ECG data, incorporated in the anatomical movement data 144, by assigning time points to the ECG electrical cycle. For example, a first time point (T1) can correlate to the P wave of the ECG electrical cycle and the depolarization of the atria. A second time point (T2) can correlate to a Q wave of the QRS complex of the ECG electrical cycle and the normal left-to-right depolarization of the interventricular septum. A third time point (T3) can correlate to a R wave of the QRS complex of the ECG electrical cycle and the early ventricular depolarization. A fourth time point (T4) can correlate to a S wave of the QRS complex of the ECG electrical cycle and the depolarization in the Purkinje fibres. The computer system can update the 3D feature by correlating each time point to a segment of the augmented representation 110, as shown in FIG. 9. The augmented representation 110 can then be animated according to this relationship, which can visually demonstrate the minimum and maximum range of movement during the cardiac cycle. Desirably, this can visually show the relation and ranges of motion for critical structures, such as an apex of the heart, chambers, valve, vessel, node, leaflet, chordae, and commissure position and orientation, septal orientation for transseptal puncture, and another structures. It should be appreciated that other anatomical features may also benefit from this application. The visual representation of these structures with dynamic and/or deformable characteristics can provide information clinically significant to assist with seating of replacement or repair products.

Spinal Procedures and Orthopedic Deformity Applications

The measuring system 106 can also be configured to measure and generate anatomical movement data 144 relating to soft tissue biomechanical forces during orthopedic deformity and spinal procedures. The measuring system 106 can be configured to measure the force via strain measurement and generated forces preoperatively and how those forces influence position and orientation of joints, long bone deformity and spinal column orientation. In certain examples, this can be performed with the measuring system 106 including the ultrasound system. The known position of a joint or bone can be measured and referenced in relation strain measurements and overall tendon or muscle length. Predictive modeling and intraoperative calculations can then be performed based on common orthopedic, deformity correction, and spinal procedures.

Ultrasound Application

As mentioned previously, the imaging system 104 can include an ultrasound system having at least one ultrasound probe 120, as shown in FIG. 2. The practitioner can move the ultrasound probe 120 over the anatomical feature 112 of the patient 114 to capture the anatomical imaging data 142, which can include the 2D images 124. FIG. 2 illustrates the ultrasound system, as the imaging system 104, with the ultrasound probe 120. The ultrasound probe 120 can be moved along the path 122 along the patient 114 to generate the 2D images 124. The 2D images 124 can then be transformed by the computer system 108 into the augmented representation 110.

In certain examples, the measuring system 106 can include the ultrasound system. The practitioner, while moving the ultrasound probe 120 over the anatomical feature 112 of the patient 114, can pause for a predetermined time at a set pause interval to account for the start and end state of respiration for the patient 114. By pausing for the predetermined time at a set pause interval, multiple phases through respiration can be captured in multiple locations and incorporated into the anatomical movement data 144. Thus, the system 100 can account for anatomical deformation and translation by updating the augmented representation 110 according to the anatomical movement data 144. For example, and with reference to FIG. 4, the augmented representation 110 can be updated to dynamically animate between two phases of the respiration of the patient 114. However, it should be appreciated that a skilled artisan can update other aspects of the augmented representation 110 according to the anatomical movement data 144.

The ultrasound system can also include a plurality of sensors. The plurality of sensors can be placed around the body of the patient 114 to account for the anatomical movement, which can include motion and respiration. The plurality of sensors can be selectively positioned to function as reference points for the generated ultrasound images. In addition, anatomical movement data 144, which can include translation and rotation data, can be generated by the plurality of sensors to enhance the augmented reality registration, overlay, and orientation by updating the augmented representation 110 according to the anatomical movement data 144.

Ultrasound Color Doppler Application

With reference to FIGS. 7-8, the measuring system 106 can include an ultrasound color doppler system. The ultrasound color doppler system can be configured to estimate the blood flow through the anatomical feature 112, such as blood vessels, by bouncing high-frequency sound waves (ultrasound) off circulating red blood cells, thereby generating anatomical movement data 144. In particular, the ultrasound color doppler can be further configured to estimate a flow direction and a velocity of the blood flow through the anatomical feature 112, which can be incorporated into the anatomical movement data 144. This can include employing color coding to designate flow direction. For example, the color blue can be used to designate that the blood is flowing away from the ultrasound probe 120 (shown as the square pattern in FIG. 8). The color red can used to show the blood is flowing towards the ultrasound probe 120 (show as the stripe pattern in FIGS. 7-8).

In certain examples, the computer system 108 can update the augmented representation 110 according to the flow direction and the velocity of the blood, incorporated as the anatomical movement data 144, to visualize the flow direction and/or the velocity of the blood flow of the anatomical feature 112. This can especially helpful when the anatomical feature 112 includes a blood vessel wall that is not echogenic or poorly imagined. Desirably, the ultrasound color doppler system can be used to dynamically register cardiac anatomy during the cardiac cycle to be used for optimal implant or repair implant deployment.

In operation, the ultrasound color doppler system, as the measuring system 106, can measure the flow direction and/or the velocity of the blood flow through the anatomical feature 112. Then, the measuring system 106 can determine and generate the associated data as the anatomical movement data 144, including how the anatomical feature 112 has moved or been changed by the cardiac cycle based on the flow direction and/or the velocity of the blood flow through the anatomical feature 112. The computer system 108 can correlate the augmented representation 110 with the anatomical movement data 144. Then, the computer system 108 can update the augmented representation 110 by adjusting the position of the augmented representation 110 to reflect the change of the position of the anatomical feature 112 by the cardiac cycle according to the anatomical movement data 144.

Method of Using the System 100

As further shown in FIGS. 10a and 10b, a method 200 may include a step 202 of providing the system 100. In a step 204, the imaging system 104 can image the anatomical feature 112 of the patient 114. The imaging system 104 can generate the anatomical imaging data 142 from the imaging of the anatomical feature 112 of the patient 114, in a step 206. In a step 208, the measuring system 106 can measure the anatomical movement of the patient 114. The measuring system 106 can generate the anatomical movement data 144 from the measuring the anatomical movement of the patient 114, in a step 210. In a step 212, the computer system 108 can receive the anatomical imaging data 142 and the anatomical movement data 144. The computer system 108 can generate the augmented representation 110 based on the anatomical imaging data 142, in a step 214. In a step 216, The computer system 108 can correlate the augmented representation 110 with the anatomical feature 112 of the patient 114. The computer system 108 can correlate the augmented representation 110 with the anatomical movement data 144 of the patient 114, in a step 218. In a step 220, the computer system 108 can render the augmented representation 110 in the augmented reality environment 116 on the augmented reality system 102. As discussed above, the computer system 108 can render the augmented representation 110 over a portion 118 of the patient 114 in the augmented reality environment 116 on the augmented reality system 102. The computer system 108 can selectively render the augmented representation 110 based on the anatomical movement data 144, in a step 222.

Now referring to FIGS. 11a and 11b, a method 200' can include a step 224' of applying post-processing to the augmented representation 110. For example, as shown in FIGS. 3-4, the computer can apply anti-aliasing to the augmented representation 110 to smooth out the jagged edges 126, which can be formed in the generation process, into the smoothed edges 128.

Advantageously, the system 100 and method can be used for dynamic registration of anatomy using augmented reality. This approach can provide a lower total procedural cost, can provide real time procedural data, and can reduce and/or eliminate radiation exposure by not having to do a CT scan to generate imaging before or during the procedure. Desirably, this disclosure can be a solution to account for dynamic body movements, such as patient 114 respiration, in the registration, correction, and dynamic motion of anatomical structures represented in an augmented reality environment 116.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A system for dynamic registration of anatomy of a patient using augmented reality, comprising:
an augmented reality system configured to display an augmented representation of an anatomical feature of the patient in an augmented reality environment;
an imaging system configured to image the anatomical feature of the patient and generate anatomical imaging data;
a measuring system configured to measure an anatomical movement of the patient and generate an anatomical movement data of internal movement of a soft tissue in the anatomy of the patient prior to performance of a surgical procedure on the patient, the anatomical movement data of internal movement of the soft tissue in the anatomy of the patient includes anatomical movement data collected over a movement cycle of the anatomy of the patient; and
a computer system in communication with the augmented reality system, imaging system, and the measuring system, the computer system configured to:
receive the anatomical imaging data from the imaging system and the anatomical movement data of internal movement of the soft tissue in the anatomy of the patient from the measuring system,
generate the augmented representation based on the anatomical imaging data,
associate the augmented representation with the anatomical feature of the patient,
correlate the augmented representation with the anatomical movement data of internal movement of the soft tissue in the anatomy of the patient,
selectively update the augmented representation based on the anatomical movement data of internal movement of the soft tissue in the anatomy of the patient, and
render the augmented representation in the augmented reality environment on the augmented reality system.

2. The system of claim 1, wherein the augmented reality system is configured to display the augmented representation over a portion of the patient in the augmented reality environment.

3. The system of claim 1, wherein the imaging system includes a member selected from a group consisting of: an ultrasound system, a computed tomography (CT) system, an electromagnetic system, a cone beam computed tomography (CBCT) system, a blood gas exchange system, a mechanically controlled ventilation system, a spirometry system, an electrocardiogram (ECG) system, a magnetic resonance imaging (MM) system, an electromechanical wave propagation system, a transesophageal echocardiogram (TEE) system, and combinations thereof.

4. The system of claim 1, wherein the imaging system is configured to image the anatomical feature of the patient and generate the anatomical imaging data prior to performance of a surgical procedure on the patient.

5. The system of claim 1, wherein the imaging system is configured to image the anatomical feature of the patient and generate the anatomical imaging data during performance of a surgical procedure on the patient.

6. The system of claim 1, wherein the measuring system includes a member selected from a group consisting of: an ultrasound system, a computed tomography (CT) system, an electromagnetic system, a cone beam computed tomography (CBCT) system, a blood gas exchange system, a mechanically controlled ventilation system, a spirometry system, an electrocardiogram (ECG) system, a magnetic resonance imaging (MM) system, an electromechanical wave propagation system, a transesophageal echocardiogram (TEE) system, and combinations thereof.

7. The system of claim 1, wherein the measuring system is configured to measure the anatomical movement and generate the anatomical movement data of internal movement of the soft tissue in the anatomy of the patient during performance of a surgical procedure on the patient.

8. The system of claim 1, wherein the computer system is further configured to smooth the augmented representation, thereby smoothing out jagged edges of the augmented representation.

9. The system of claim 1, the computer system is configured to update the augmented representation by updating a position of the anatomical feature of the patient, thereby compensating for a movement of the anatomical feature according to the anatomical movement data of internal movement of the soft tissue in the anatomy of the patient.

10. The system of claim 1, the computer system is configured to update the augmented representation by updating a structure of the augmented representation, thereby showing structural changes of the augmented representation according to anatomical movement data of internal movement of the soft tissue in the anatomy of the patient.

11. The system of claim 1, the computer system is configured to update the augmented representation by updating at least one of a position of the anatomical feature and a structure of the augmented representation by animating a transition between an original state of the augmented representation and the updated state of the augmented representation.

12. The system of claim 1, wherein the computer system is configured to selectively update the augmented representation based on the anatomical movement data of internal movement of the soft tissue in the anatomy of the patient at a predetermined interval.

13. The system of claim 1, wherein the computer system is configured to selectively update the augmented representation in response to an input.

14. The system of claim 1, wherein the anatomical movement data includes multiple cycles of the anatomical movement.

15. The system of claim 14, wherein an average of the multiple cycles of the anatomical movement data is calculated.

16. A method for dynamic registration of autonomy of a patient using augmented reality, the method comprising the steps of:
providing a system for dynamic registration of anatomy using augmented reality having an augmented reality system, an imaging system, a measuring system, and a computer system;
imaging, by the imaging system, an anatomical feature of the patient;
generating, by the imaging system, anatomical imaging data from imaging the anatomical feature of the patient;
measuring, by the measuring system, an anatomical movement of the patient prior to performance of a surgical procedure on the patient, the anatomical movement data of internal movement of the soft tissue in the anatomy of the patient includes anatomical movement data collected over a movement cycle of the anatomy of the patient;
generating, by the measuring system, anatomical movement data of internal movement of a soft tissue in the anatomy of the patient from measuring the anatomical movement of the patient;
receiving, by the computer system, the anatomical imaging data and the anatomical movement data of internal movement of the soft tissue in the anatomy of the patient;
generating, by the computer system, an augmented representation based on the anatomical imaging and positional data;
associating, by the computer system, the augmented representation with the anatomical feature of the patient;
correlating, by the computer system, the augmented representation with the anatomical movement data of internal movement of the soft tissue in the anatomy of the patient of the patient;
selectively updating, by the computer system, the augmented representation based on the anatomical movement data of internal movement of the soft tissue in the anatomy of the patient; and
rendering, by the computer system, the augmented representation in an augmented reality environment on the augmented reality system.

17. The method of claim 16, wherein the measuring system includes an ultrasound system having an ultrasound probe, whereby 2D images are captured by moving the ultrasound probe over the anatomical feature of the patient and pausing for a predetermined time at a set pause interval.

18. The method of claim 16, wherein the measuring system includes a spirometry system, and wherein the anatomical movement data of internal movement of the soft tissue in the anatomy of the patient includes a flow volume loop having a plurality of reference points that correlate a position of the augmented representation with a known volume of air in lungs of the patient.

19. The method of claim 16, wherein the measuring system includes an electrocardiogram (ECG) system, and wherein the anatomical movement data of internal movement of the soft tissue in the anatomy of the patient includes an ECG electrical cycle having a plurality of components, and each one of the components correlates to a segment of the augmented representation.

20. The method of claim 16, further including a step of applying post-processing to the augmented representation to smooth the augmented representation, thereby smoothing out jagged edges of the augmented representation.

* * * * *